United States Patent [19]

Neumann et al.

[11] Patent Number: 5,475,163
[45] Date of Patent: Dec. 12, 1995

[54] PROCESS FOR THE PREPARATION OF 2,3-DICHLORO-NITROBENZENE

[75] Inventors: Karl H. Neumann, St. Augustin; Wolfram Kissener, Neunkirchen/Seelscheid; Helmut Fiege, Leverkusen, all of Germany

[73] Assignee: Bayer Aktiengesellschaft, Leverkusen, Germany

[21] Appl. No.: 369,560

[22] Filed: Jan. 6, 1995

Related U.S. Application Data

[63] Continuation of Ser. No. 96,122, Jul. 22, 1993, abandoned.

[30] Foreign Application Priority Data

Jul. 29, 1992 [DE] Germany .......................... 42 25 023.4

[51] Int. Cl.$^6$ ................................................. C07C 205/06
[52] U.S. Cl. ............................................ 568/937; 568/938
[58] Field of Search ..................................... 568/937, 938

[56] References Cited

U.S. PATENT DOCUMENTS

| | | | |
|---|---|---|---|
| 3,957,889 | 5/1976 | Milligan et al. | 568/937 |
| 3,979,467 | 9/1976 | Schumacher . | |
| 4,420,645 | 12/1983 | Vaidyanathan | 568/937 |
| 4,453,027 | 6/1984 | Vaidyanathan . | |
| 4,476,335 | 10/1984 | Takenaka et al. . | |

FOREIGN PATENT DOCUMENTS

| | | |
|---|---|---|
| 2422306 | 11/1974 | Germany . |
| 2422305 | 11/1974 | Germany . |
| 3244293 | 7/1983 | Germany . |
| 9211227 | 7/1992 | WIPO . |

OTHER PUBLICATIONS

Pine et al., "Organic Chemistry", 4th Ed. (1980) McGraw–Hill Books, N.Y., pp. 607–618.
Chemical Abstracts, vol. 81, No. 15, 140CT74, Columbus, Ohio, abstract No. 90730n, p. 400, (1974).

*Primary Examiner*—Robert W. Ramsuer
*Assistant Examiner*—John Peabody
*Attorney, Agent, or Firm*—William C. Gerstenzang; Sprung Horn Kramer & Woods

[57] ABSTRACT

2,3-dichloro-nitrobenzene can be prepared by nitration of 1,2-dichlorobenzene using an anhydrous mixture of phosphoric acid, sulphuric acid and nitric acid. The conditions according to the invention displace the ratio of 2,3,-dichloro-nitrobenzene and 3,4-dichloro-nitrobenzene in favor of the 2,3-isomer.

9 Claims, No Drawings

PROCESS FOR THE PREPARATION OF 2,3-DICHLORO-NITROBENZENE

This application is a continuation, of application Ser. No. 08/096,122, filed on Jul. 22, 1993, now abandoned.

BACKGROUND OF THE INVENTION

The invention relates to a process for the preparation of 2,3-dichloro-nitrobenzene by nitration of 1,2-dichloro-benzene using an anhydrous mixture of nitric acid, sulphuric acid and phosphoric acid as the nitrating medium.

Dichloro-nitrobenzenes are important intermediates for the synthesis of pharmaceuticals and plant protection agents. The currently known processes for the nitration of 1,2-dichlorobenzene give a mixture of 2,3-dichloro-1-nitrobenzene and 3,4-dichloro-1-nitrobenzene. The market demand for the two compounds is subject to changes. Thus, there was a greater need hitherto for the 3,4-isomer. Under the nitrating conditions practised hitherto the formation of this isomer was favoured so that production could follow the market demand.

In the meantime however, the market demand for the 2,3-isomer has increased. In order to be able to satisfy this increased demand, without simultaneously producing additional 3,4-isomer, a production procedure is necessary with which the formation of the two isomers can be controlled, and with which in particular the production of the 2,3-isomer, which has hitherto been obtained in a great deficiency, can be increased compared with the 3,4-isomer.

The use of phosphoric acid in the nitrating acid mixture is already known from the nitration of monochlorobenzene, in order to influence the ratio of the two isomers, namely of 2-chloro- and of 4-chloro-nitrobenzene.

Thus, DE-OS (German Published Specification ) 2,422,305 describes a process in which the reaction is carried out using 90% strength nitric acid as the nitrating agent and in a nitrating medium consisting of phosphoric acid and sulphuric acid. Using this process, the ratio of the para to the ortho isomer can be shifted from 1.63 to 1.2. The said DE-OS ( German Published Specification ) '305 does not indicate a concentration of the phosphoric acid; it may therefore be suspected that commercially available, 85% strength by weight phosphoric acid is used. In addition, the said DE-OS (German Published Specification) '305 does not give any yields and any data for dinitration. According to our own investigations, the yields according to this process are only about 80% of the theoretical yield.

Yield data (up to 93%) are found in DE-OS (German Published Specification) 2,422,306, which is obviously an improvement in the process of DE-OS (German Published Specification) '305. To this end, a metal catalyst, for example one composed of molybdenum, manganese, vanadium or tungsten, is added to the acidic nitrating medium.

However, such a process brings serious disposal problems with it.

Both specifications, namely DE-OS (German Published Specification) '305 and DE-OS (German Published Specification) '306 contain no data whatsoever about a possible transfer of the processes described therein to dichlorobenzenes, especially to 1,2-dichlorobenzene.

Another process, which has been published in DE-OS (German Published Specification) 3,244,293, is also directed to the nitration of monochlorobenzene. In this, nitration is carried out in a nitrating medium which consists only of phosphoric acid, with at most one mol of nitric acid per mole of chlorobenzene. The phosphoric acid employed is employed in concentrated form with a $P_2O_5$ content of more than 72.4% by weight. Sulphuric acid is completely dispensed with. According to the description of this DE-OS (German Published Specification) '293, a para/ortho ratio of the chloronitrobenzenes of 0.9 can be obtained. The yields, relative to the nitric acid employed, are very high if the nitric acid is employed in a relatively large deficit. However, is simultaneously means incomplete reaction of the chlorobenzene. Such an inadequate conversion is only justifiable with economical starting materials, such as monochlorobenzene, and moreover presents recycling problems. This DE-OS (German Published Specification) '293 also gives no indication at all of whether the process described therein can be transferred to other substrates, such as dichlorobenzenes, especially to 1,2-dichlorobenzene.

The restriction of the process descriptions mentioned to monochlorobenzene is therefore understandable, in that dichlorobenzenes are basically slow to react owing to the deactivating effect of the second halogen atom, the competing directing effect of two substituents being added as an additional difficulty. The need therefore existed for a process for the preparation of 2,3-dichloro-nitrobenzene, which gives high yields and at the same time offers the possibility of satisfying an increased demand for 2,3-dichloro-nitrobenzene.

SUMMARY OF THE INVENTION

A process for the preparation of 2,3-dichloro-nitrobenzene by nitration of 1,2-dichlorobenzene with nitric acid has been found, which is characterised in that an anhydrous mixture of phosphoric acid, sulphuric acid and nitric acid is employed for the nitration.

DETAILED DESCRIPTION OF THE INVENTION

If nitration is carried out in the hitherto known manner in an $HNO_3/H_2SO_4$ mixture without addition of $H_3PO_4$, in the nitration of 1,2-dichlorobenzene the two isomers are typically formed in approximately 98.5% yield in a ratio of 3,4-dichloro- 1-nitrobenzene to 2,3-dichloro- 1-nitrobenzene of 8.2:1. If 1,2-dichlorobenzene is nitrated using phosphoric acid which is concentrated to 104%, simultaneously dispensing with sulphuric acid and with additional use of nearly anhydrous nitric acid, then a shift in favour of the 2,3-isomer is obtained. The ratio 3,4-: 2,3-dichloro-1-nitrobenzene accordingly falls to values of 5.95 or 5.45, depending slightly on the reaction temperature, as was found by our own experiments. The term 104% strength $H_3PO_4$ signifies a concentrated, i.e. dehydrated, phosphoric acid, which contains a proportion of pyrophosphoric acid and accordingly has a $P_2O_5$ content which corresponds to 104% $H_3PO_4$. The serious disadvantage of such a procedure is the great fall in the yield to 89% or even 86% as a specific function of the reaction temperature.

It is surprising then that even a small addition of sulphuric acid to the reaction medium maintains the favourable isomer ratio or even additionally slightly improves it, but at the same time brings the total yield to values far above 90%, in many cases above 95% of the theoretical yield.

The process according to the invention is characterised by the use of an anhydrous nitrating acid mixture. Such a nitrating acid mixture can be prepared by mixing together industrially available, nearly anhydrous acids, provided one of the acids is employed with an anhydride content which is suitable to use up the small water content of the two other acids. Thus, the reaction can be carried out, for example, by use of a 98% strength $HNO_3$ and a 98% strength $H_2SO_4$ if the phosphoric acid is an acid which has been concentrated in the manner described above, which thus contains a proportion of pyrophosphoric acid, which corresponds to a content of acid anhydride $P_2O_5$ which exceeds the content of the 100% strength $H_3PO_4$. However, it is likewise conceivable that a nitric acid and a phosphoric acid with a low water content are employed, if at the same time, instead of the sulphuric acid, oleum is employed whose content of $SO_3$ is suitable to use up the water entrained by the other acids. Of course, it is furthermore possible to employ a more highly water-containing. $HNO_3$ if the phosphoric acid is employed in the form of the concentrated acid and/or the sulphuric acid in the form of oleum. Further modifications of this composition of the nitrating acid mixture are known in expert manner when only the indication of the freedom from water in the acid mixture is fulfilled.

In a preferred manner, the nitric acid and the sulphuric acid are employed as industrially available approximately 98% strength acids and the phosphoric acid is employed in the form of a concentrated acid. It is self-evident that phosphoric acid and/or sulphuric acid with a content of anhydride can also be employed in the manner described above in an amount which exceeds the consumption of the water entrained by the other acid (the other acids). Such a nitrating acid mixture, which still contains a proportion of anhydride in the form of pyrophosphoric acid is also an anhydrous acid mixture within the meaning of the present invention.

The molar mixing ratio of sulphuric acid and phosphoric acid assumes values from 0.05 to 3 mol of $H_2SO_4$: 1 mol of $H_3PO_4$, preferably 0.1 to 1.5 mol of $H_2SO_4$: 1 mol of $H_3PO_4$, very particularly preferably from 0.12 to 0.5 mol of $H_2SO_4$: 1 mol of $H_3PO_4$.

The process according to the invention is carried out at a reaction temperature of 30 to 180° C., preferably 60 to 140° C. particularly preferably 75 to 125° C. In this connection, it has been found that the proportion of 2,3-dichloro-nitrobenzene compared to 3,4-dichloronitrobenzene at higher temperature is greater than at lower temperature within the range indicated. In the case of this change in the isomer composition, the yield on the whole is only insignificantly reduced.

The molar ratio of the nitric acid to the dichlorobenzene is 0.7 to 1.4: 1, preferably 0.85 to 1.3: 1, very particularly preferably 1.0 to 1.2: 1.

After completion of the nitration, a phase separation in general occurs into an upper organic phase and a lower acid phase. After removal of the organic phase, the isomer mixture of 2,3-dichloro-nitrobenzene/3,4-dichloro-nitrobenzene contained therein is worked up by means of further aqueous work-up (removal of residual acid) and separated into the two isomers by customary methods, such as distillation, crystallisation or chromatography. It is, then, a further advantageous variant of the process according to the invention that the lower acid phase obtained in this work-up can be freed from the water of reaction from the nitration reaction by distillation, preferably under reduced pressure, and as a result an anhydrous mixed acid, consisting essentially of sulphuric acid and phosphoric acid, can again be prepared. In a particularly preferred manner, in this connection the removal of water is driven on so far that the mixture again contains proportions of anhydride (e.g. in the form of pyrophosphoric acid). Hereupon, the spent nitric acid and the small residual amounts of acid which have remained in the product phase are replaced, whereupon this nitrating acid mixture is again ready for use.

In the case in which a marked separation into an organic product phase and an inorganic mixed acid phase does not occur, this can be effected by addition of a little water.

It is possible to carry out the process according to the invention batchwise or continuously.

The following examples illustrate the process according to the invention without restricting it to these examples.

EXAMPLE 1 (for comparison)

1.36 mol of 1,2-dichlorobenzene were introduced into 1.64 mol of 80.5% strength $H_2SO_4$. A mixture of 1.38 mol of 98% strength $HNO_3$ and 1.31 mol of 98% strength $H_2SO_4$ was added dropwise at 45 to 50° C. in the course of 1.5 h with rapid stirring. The mixture was then stirred at 45° to 50° C. for a further 2 h. The organic phase was removed from the aqueous phase while still warm and washed until neutral with dilute $Na_2CO_3$ solution and $H_2O$.

This experiment shows the result of a nitration process which is customary today in industry.

| Yield | 3,4-isomer | 2,3-isomer | starting material | f = 3,4/2,3 |
|---|---|---|---|---|
| 98% of theory | 88.4% | 10.8% | 0.8% | 8.2 |

EXAMPLES 2 to 3 (for comparison)

The process of Example 1 was repeated with the difference that the 80.5% strength or 98% Strength $H_2SO_4$ was replaced by 1.64 mol or 1.31 mol of $H_3PO_4$ concentrated to 104% (fictitious $H_3PO_4$ content as a result of removal of $H_2O$ and formation of $H_4P_2O_7$) and the nitration temperature was increased to 85 to 110° C.

| No. | T (°C.) | Yield | 3,4-isomer | 2,3-isomer | Starting material | f (3,4/2,3) |
|---|---|---|---|---|---|---|
| 2) | 85 | 89.4% | 79.01 | 13.28 | 7.71 | 5.95 |
| 3) | 105–110 | 86.1% | 76.81 | 13.87 | 9.32 | 5.54 |

EXAMPLES 4 to 6

1.36 mol of 1,2-dichlorobenzene were introduced into a mixture of 0.42 mol of 98% strength $H_2SO_4$ and 1.411 mol of $H_3PO_4$ concentrated to 104%. A nitrating acid mixture of 1.38mol of 98% strength $HNO_3$, 0.327 mol of 98% strength $H_2SO_4$ and 1.127 mol of 104% strength $H_3PO_4$ was added dropwise with good stirring at reaction temperatures from 85° C to 125° C in the course of 1.5 h. The mixture was stirred at 85° C. to 125° C. for a further 2 h and the aqueous phase was then removed from the organic phase while still warm. The organic phase was washed until neutral with dilute $Na_2CO_3$ solution and $H_2O$.

| No. | T (°C.) | Yield | 3,4-isomer | 2,3-isomer | Starting material | f (3,4/2,3) |
|---|---|---|---|---|---|---|
| 4) | 85 | 96.6% | 83.50 | 14.15 | 2.35 | 5.89 |
| 5) | 105–110 | 93.7% | 80.49 | 14.80 | 4.71 | 5.44 |
| 6) | 125 | 91.9% | 79.46 | 15.12 | 5.42 | 5.25 |

EXAMPLES 7 to 12

1.36 mol of o-dichlorobenzene were introduced into a mixture of 0.38 mol of 98% strength $H_2SO_4$ and 1.305 mol of 104% strength $H_3PO_4$. At a temperature of 105° to 110° C., a nitrating acid mixture of 1.38 mol of 98% strength $HNO_3$, 0.38 mol of 98% strength $H_2SO_4$ and 1.305 mol of 104% strength $H_3PO_4$ was added dropwise in the course of 1.5 h with rapid stirring. The mixture was then stirred for a further 2 h at the same temperature. The organic phase was removed from the acid phase while still warm and washed with dilute $Na_2CO_3$ solution and $H_2O$. The aqueous phases were extracted with $CH_2Cl_2$ and the combined organic phase was concentrated.

The acid phase was then subjected to incipient distillation at 20 mm Hg column up to a bottom temperature of 180° C. and then temperature-controlled for 3 h. The loss in the concentrated waste acid was compensated by addition of fresh 104% strength $H_3PO_4$ and the acid worked up in this way was employed again in the next nitration.

a phosphoric acid concentrated to over 72.4% by weight of $P_2O_5$ is employed.

3. The process of claim 1, wherein the molar mixing ratio of sulphuric acid and phosphoric acid assumes values from 0.1 to 1.5 mol of $H_2SO_4$: 1 mol of $H_3PO_4$.

4. The process of claim 3 wherein the molar mixing ratio of sulphuric acid and phosphoric acid assumes values of 0.12 to 0.5 mol of $H_2SO_4$: 1 mol of $H_3PO_4$.

5. The process of claim 1, wherein the nitration is carried out at a reaction temperature of 60° to 140° C.

TABLE 3

| No. | Acid initially introduced | Acid added dropwise | Yield (%) | 3,4-isomer | 2,3-isomer | Starting material | f (3,4/2,3) |
|---|---|---|---|---|---|---|---|
| 7) | 0.38 mol of $H_2SO_4$ 1.305 mol of $H_3PO_4$ | 0.38 mol of $H_2SO_4$ 1.305 mol of H3PO4 | 94.3 | 81.30 | 14.96 | 3.74 | 5.43 |
| 8) | recycl. | recycl. | 94.8 | 81.39 | 14.91 | 3.70 | 5.46 |
| 9) | recycl. | recycl. | 94.7 | 81.57 | 14.83 | 3.60 | 5.50 |
| 10) | recycl. | recycl. | 95.2 | 81.63 | 14.90 | 3.47 | 5.47 |
| 11) | recycl. | recycl. | 95.4 | 82.14 | 14.92 | 2.94 | 5.50 |
| 12) | recycl. | recycl. | 96.0 | 82.00 | 14.92 | 3.08 | 5.49 |

What is claimed is:

1. A process for the preparation of 2,3-dichloro-nitrobenzene by nitration of 1,2-dichlorobenzene with nitric acid, wherein an anhydrous mixture of phosphoric acid, sulphuric acid and nitric acid is employed for the nitration; the molar mixing ratio of sulphuric acid and phosphoric acid assumes values from 0.05 to 3 mol of $H_2SO_4$:1 mol of $H_3PO_4$; the nitration is carried out at a reaction temperature of 30° to 180° C.; and the nitric acid is employed in a molar ratio of 0.7 to 1.4, relative to the 1 mol of 1,2-dichloro-benzene.

2. The process of claim 1, wherein in addition to nearly anhydrous nitric acid and nearly anhydrous sulphuric acid, 6. The process of claim 5 wherein the nitration is carried out at a reaction temperature of 75° to 125° C.

7. The process of claim 1, wherein the nitric acid is employed in a molar ratio of 0.85 to 1.3, relative to 1 mol of 1,2-dichloro-benzene.

8. The process of claim 7, wherein the nitric acid is employed in a molar ratio of 1.0 to 1.2, relative to 1 mol of 1,2-dichloro-benzene.

9. The process of claim 1, wherein the acid mixture obtained in the product work-up is freed from water by distillation and recycled.

* * * * *